United States Patent
Philippi et al.

(10) Patent No.: US 8,501,075 B2
(45) Date of Patent: Aug. 6, 2013

(54) METHOD FOR MANUFACTURING A THREE-DIMENSIONAL OBJECT

(75) Inventors: Jochen Philippi, Gräfelfling (DE); Alexander Schilling, München (DE)

(73) Assignee: EOS GmbH Electro Optical Systems, Krailling (DE)

( * ) Notice: Subject to any disclaimer, the term of this patent is extended or adjusted under 35 U.S.C. 154(b) by 232 days.

(21) Appl. No.: 12/953,856

(22) Filed: Nov. 24, 2010

(65) Prior Publication Data

US 2011/0121492 A1    May 26, 2011

(30) Foreign Application Priority Data

Nov. 25, 2009  (DE) .......................... 10 2009 055 661

(51) Int. Cl.
*B29C 35/08*  (2006.01)
*B29C 41/02*  (2006.01)
*B29C 41/52*  (2006.01)

(52) U.S. Cl.
USPC .......... 264/401; 264/40.1; 264/406; 264/407; 264/463; 264/497

(58) Field of Classification Search
USPC ................ 264/40.1, 113, 308, 401, 406, 407, 264/460, 463, 497
See application file for complete search history.

(56) References Cited

U.S. PATENT DOCUMENTS

| | | | |
|---|---|---|---|
| 5,659,478 A | 8/1997 | Pennisi et al. | |
| 2004/0254665 A1* | 12/2004 | Fink et al. | 264/497 X |
| 2005/0274197 A1* | 12/2005 | Le | 73/801 |

FOREIGN PATENT DOCUMENTS

| | | | |
|---|---|---|---|
| DE | 195 02 756 A1 | 8/1996 | |
| EP | 1 486 317 A1 | 12/2004 | |
| JP | 03243845 A | * 10/1991 | |

OTHER PUBLICATIONS

DIN EN ISO 6721-3:1996, Kunststoffe, Bestimmung dynamisch-mechanischer Eigenschaften {German} Partial translation (English).
Bai et al., "Acoustical Test Instrument of Mechanical Properties with Shaft Work pieces", Journal of Physics: Conference Series 48 (2006) 629-634.
Bono et al., "Resonant Inspection As an Automated NDT Method for Sinter Brazed Powder Metal Components", SAE International, 2007.

* cited by examiner

*Primary Examiner* — Leo B Tentoni
(74) *Attorney, Agent, or Firm* — Seyfarth Shaw LLP

(57) ABSTRACT

Method of manufacturing a three-dimensional object according to which the object is built layer-wise by solidification of a building material, wherein a test specimen is built which is excited to oscillate after being built and wherein natural frequencies of the oscillations are determined.

18 Claims, 3 Drawing Sheets

361Hz    485Hz    610Hz

496Hz    620Hz    745Hz

METHOD FOR MANUFACTURING A THREE-DIMENSIONAL OBJECT

BACKGROUND OF THE INVENTION

The invention relates to a method of manufacturing a three-dimensional object. Especially, the invention relates to a method of laser sintering of members.

Increasingly, selective laser sintering is not only used for the manufacturing of prototypes or of small series of members, but also for the series production of fully operative members. As a rule, the manufactured members have to undergo quality tests, especially in order to test their mechanical properties. The mechanical properties of members, for example the coefficient of elasticity, however, are difficult to measure up to the present, because the necessary equipment is a complex one.

It is known to the applicant that test specimen, for example tensile bars, can be manufactured by the laser sintering method and can be mechanically measured afterwards in order to derive information about the properties, for example the coefficient of elasticity of a member to be produced, which properties may be dependent on the manufacturing conditions in the laser sintering process and from the material.

It is known from EP 1 486 317 A1 to co-manufacture at least one iterative improvement specimen, which can comprise, for example, Z-tensile arrays, density cubes, dimensional pyramids, flexural samples and combinations thereof, together with the member to be manufactured. Then, by means of destructive testing of the iterative improvement specimens, there are obtained data sets for an optimal manufacture of the production parts themselves using an iterative method. The above method is, however, quite complex.

BRIEF SUMMARY OF THE INVENTION

It is an object of the invention to provide a method of manufacturing a three-dimensional object, especially a laser sintering method, which allows a simple, rapid and precise detection of especially mechanical properties of the members.

Further characteristics and objects of the invention will arise from the description of embodiments thereof based on the drawings, of which:

DETAILED DESCRIPTION OF THE INVENTION

Figure 1:
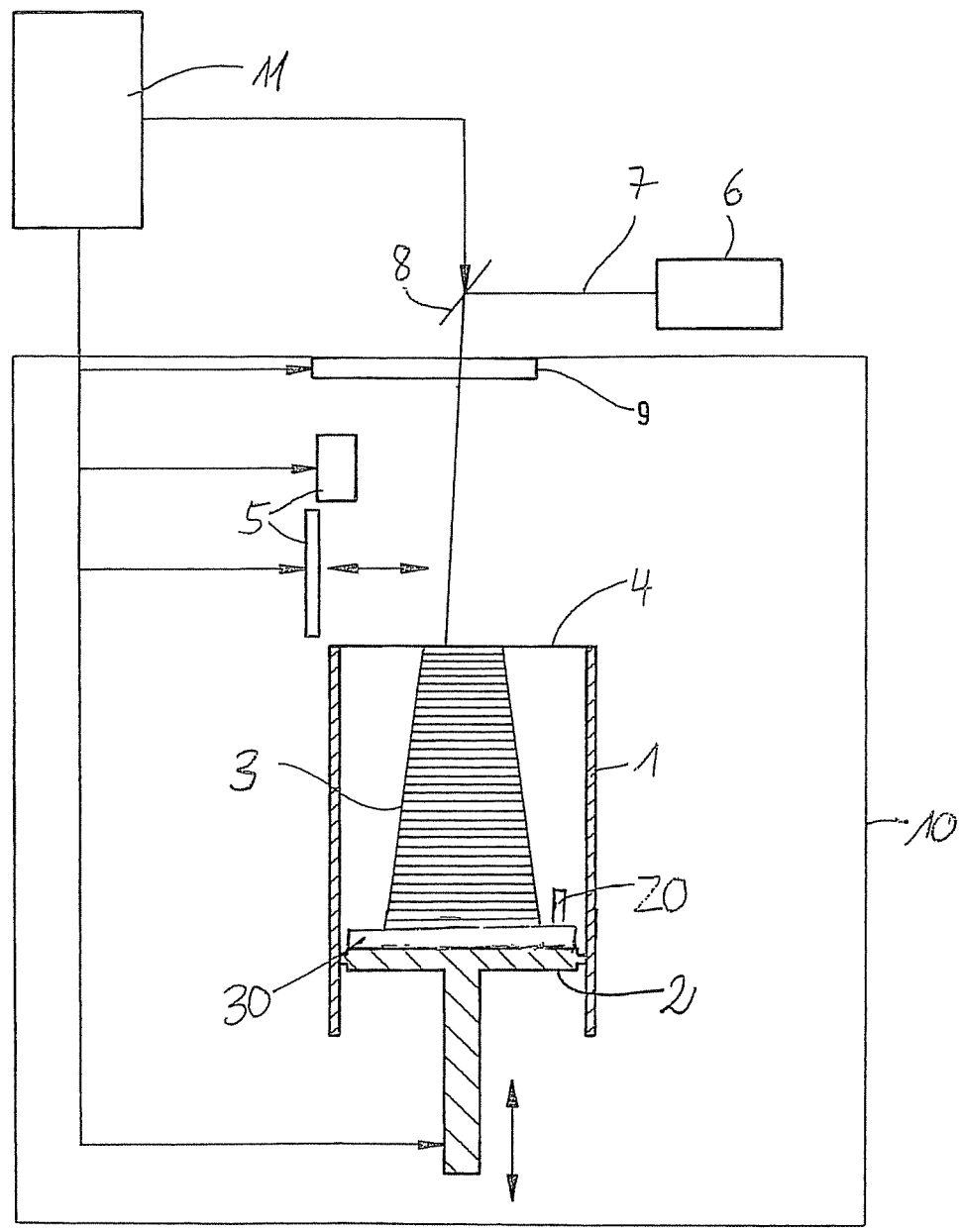
FIG. 1 shows a schematic representation of a laser sintering device as an example of a device for manufacturing a three-dimensional object.

In FIG. 1, there is shown a laser sintering device as an example for a device for layer-wise manufacturing a three-dimensional object by means of a generative production method. The device comprises a container 1 open to the top with a support 2 movable therein in vertical direction that supports the object to be formed and defines a building area. The support 2 is adjusted in vertical direction so that the respective layer to be solidified of the object lies within a working plane 4. Furthermore, there is provided an application device 5 for applying a powdery building material which can be solidified by electromagnetic radiation. As a source of the electromagnetic radiation, there is provided a laser 6. A laser beam 7 generated by the laser 6 is directed onto an injection window 9 by a deflection device 8, and is passed therethrough into the building chamber 10 and is focussed on a predefined point in the working plane. Moreover, there is provided a control unit 11 by which the components of the device are controlled for executing the manufacturing process in a coordinated manner. The control is effected, inter alia, depending on CAD data of the object to be produced.

As the powdery building material, all powders and powder mixtures, respectively, suitable for the laser sintering process may be used. Such powders comprise, for example, plastic powders like polyamide or polystyrene, PEEK, metallic powders as stainless steel powders or other metallic powders adapted for the respective purpose, especially alloys, plastic-coated sand or ceramic powder. The operation of the laser sintering device is effected in a way so that the application device 5 moves over the building area and applies a powder layer in a predefined thickness. Subsequently, a cross section of the object 3 of the respective layer is irradiated by the laser beam, and the powder there is solidified. Then, the support 2 is moved downwards and a new powder layer is applied. In this manner, the manufacture of the object 3 is effected layer-wise. After completion, the object is removed and undergoes a finishing treatment, if applicable, and/or undergoes a quality control.

In the method according to the present invention according to a first embodiment, as depicted schematically in FIG. 1, a test specimen 20 is co-built when building the object 3 to be produced itself. This test specimen 20 is excited to oscillations after the manufacture of the object 3, and then, the natural frequencies of the oscillating specimen 20 are determined. From those ones, properties of the manufactured object 3, for example the coefficient of elasticity, are determined. The CAD data which contain the geometry of the test specimen, may be contained in the same data set which also contains the object data, or the CAD data can be chosen, for example from a library, and added.

The test specimen 20 can be built anywhere at a suitable place in the building space defined by the container wall and the support. There is no need to connect it to the support 2 and/or the object 3. According to a preferred embodiment of the method, the test specimen 20 is not built freely in the building space, but on a base 30 that is detachably connected to the support 2. The specimen 20 as well as the object 3 to be produced is connected to the base 30, which is taken out of the device together with the object and the test specimen after completion of the object. The object 3 can, for example, be connected to the detachably secured base 30 via support structures (not shown) having predetermined breaking points, so that, after removal of the base, the object may simply be separated with the test specimen 20 remaining on the base 30. This proceeding is especially suitable for sintering of metal powders.

Subsequently, the test specimen 20 is mechanically excited to oscillations. The excitation of the test specimen may be effected, for example, by hand strikes in the desired oscillation direction or within an automatic test stand. The developing natural oscillations of the test specimen 20 are then determined by means of an acoustic or optic method, as described further below. Due to the fact that in the preferred embodiment the test specimen 20 is connected to the base, there is no necessity of clamping the test specimen. The mass of the base 30 is such that the natural oscillations of the test specimen are not influenced by it. At reference measurements, for example when comparing a measured frequency with the frequency of a reference specimen, otherwise identical measuring conditions, for example as to temperature etc., are used.

The test specimen is preferably a body having a simple geometry, and especially it has only one or few dominant natural frequency modes. In the embodiment shown, the test specimen is formed as a flat bar or beam having an essentially orthogonal cross section which comprises, as can be seen from FIGS. 2 and 3, a height z and a thickness y as well as a width x. The flat bar has a width x which exceeds the thickness y.

Figure 2:
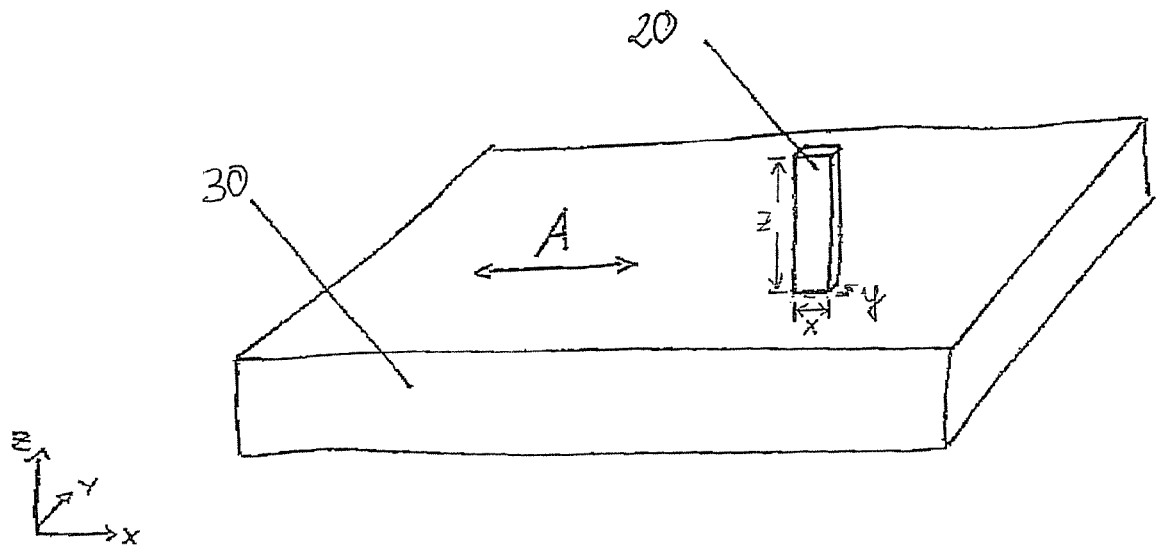
FIG. 2 shows an enlarged representation of a test specimen on a building platform for a laser sintering device as an example for an embodiment of the manufacturing process.
Figure 3:
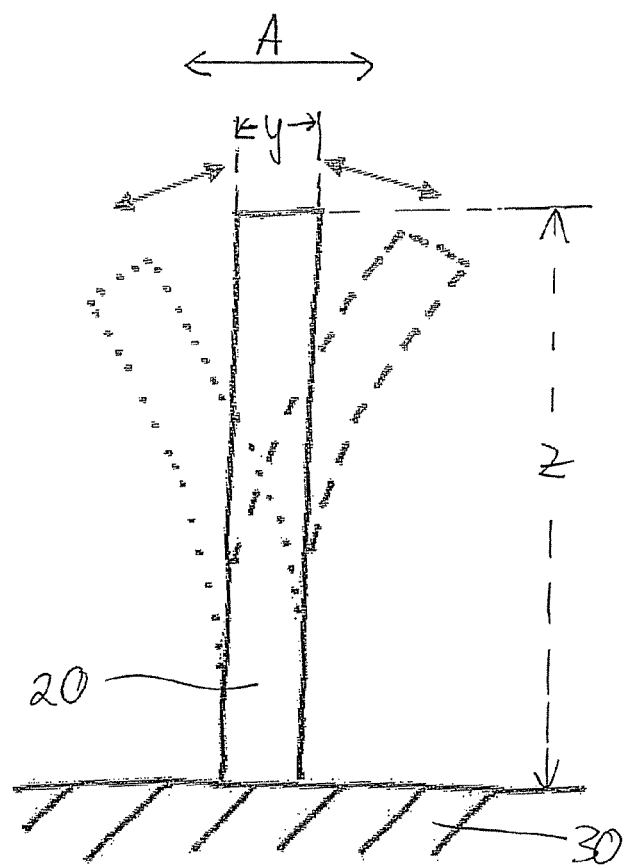
FIG. 3 shows an enlarged section from FIG. 2 comprising schematically indicated oscillations of the test specimen.

The application device applies a new layer by turns when moving over the building area in one direction and in the opposed direction, respectively. In FIG. 2, the direction A in which the application device applies the powder material when moving over the building area, is marked by a double arrow. The orientation of the test specimen 20 on the base 30 is such that the main oscillation direction shown in FIG. 3 is orthogonal or essentially orthogonal to the application direction in the application plane. The flat bar shown is preferably built as a test specimen in such a manner that its narrow side is oriented in the application direction.

Figure 4:
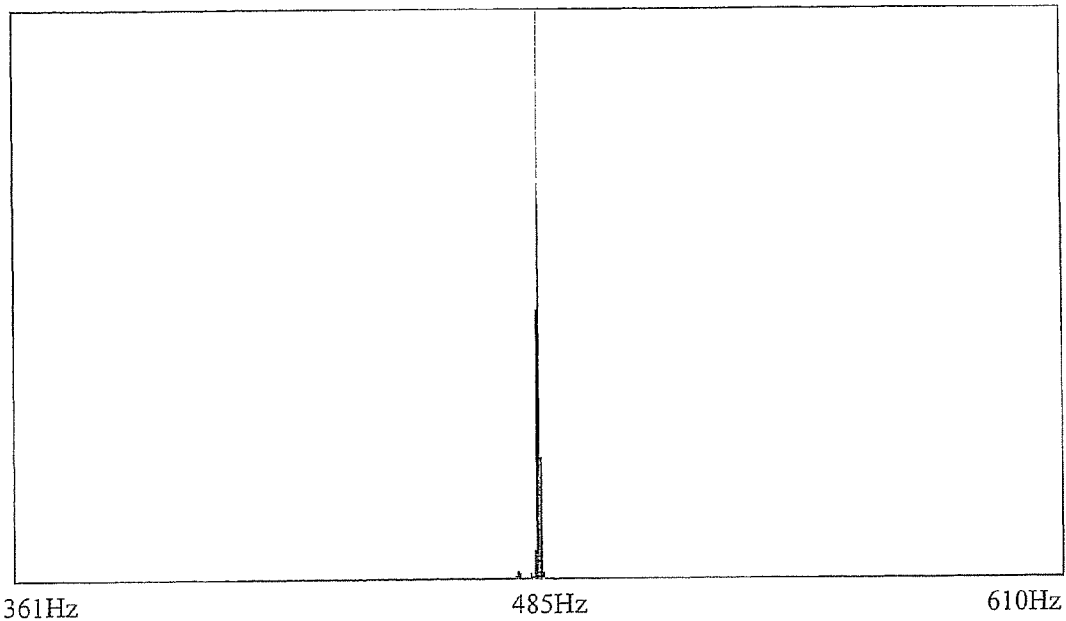
FIG. 4 shows a frequency diagram with a first natural frequency of the test specimen according to FIG. 3.
Figure 5:
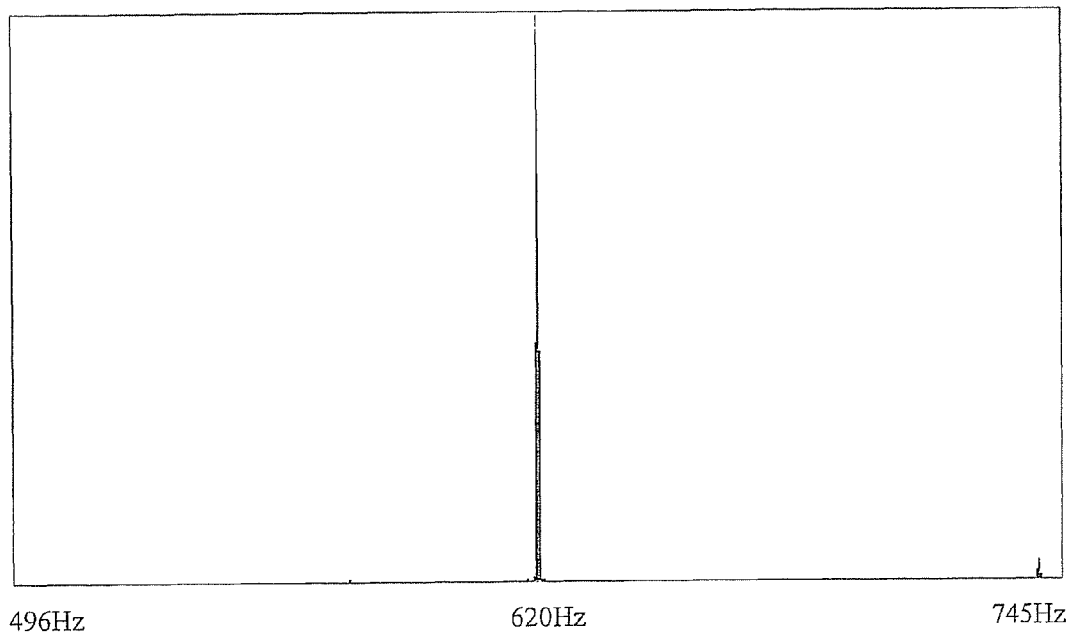
FIG. 5 shows an exemplary frequency diagram of a second test specimen.

In the acoustic determination of the natural frequencies, the sound sequences produced by the oscillations of the test specimen are recorded and analyzed. For example, an audio data file may be recorded digitally and analyzed by a conventional spectrum analysis, whereby the frequencies of the natural oscillations are obtained. In FIGS. 4 and 5, there are shown sections of a frequency diagram exemplary for a flat bar as test specimen 20 and laser sintering of metal powder. The natural frequencies may lie in the range up to about 5.000 Hz, however, good results are achieved especially in the range of less than 1.000 Hz. Those are, in case of identical dimensions, a measure for the material properties, as for example the density and the rigidity, and for the dimensional deviations, respectively, of the members. A higher rigidity leads to a higher frequency, an increase of the density or of the dimensions leads to a decrease of the frequency. For ideally elastic beams, the natural frequency is defined as follows:

$$f_1 = c_1 \cdot \sqrt{\frac{E}{\rho}}$$

mit $$c_1 = \frac{3{,}52}{4\pi \cdot \sqrt{3}} \cdot \frac{y}{z^2}$$

with ρ being the density of the beam, z the height and y the thickness of the beam. E is the coefficient of elasticity. For an ideally elastic beam, the natural frequency essentially does not depend on the width x. For this reason, in case that the test specimen 20 is formed as an essentially ideal elastic beam, as it is shown in FIGS. 2 and 3, it is possible to select the width of the beam x to be relatively large, so that the test specimen is not damaged if the application device applies a new layer.

By means of the determination of the natural frequencies it is possible to derive a plurality of properties, especially of the test specimen, however, in the consequence also of the object produced. For specimens of simple geometries, it is possible to infer directly from the dimensions and a density measurement out of the frequency measurement on the coefficient of elasticity E of the building material used. In case of more complex test specimens, e.g. bell shaped ones, properties can be determined making use of a finite element program for the analysis of natural modes. Deviations of the frequency in comparison to a reference specimen measured in advance also arise in case of inhomogeneity of the material, material aging, eccentricities, cracks, bonding defects and so on. It is also imaginable to draw conclusions on coating defects in one or several layers.

According to the first embodiment of the method, a quality assessment of the produced object is carried out on the basis of the measurement of the natural frequencies of a co-built test specimen of simple geometry. The results can serve for evaluation of the produced object as to its properties and thus as to its quality, and for carrying out corrective measures when building the next object, where appropriate.

According to a variation of the first embodiment, the determination of the natural frequencies is not effected acoustically, but optically. For this purpose the oscillation of the test specimen is recorded, for example by means of a contactless velocity measurement device, and thereafter analyzed by means of known methods in order to obtain the natural frequencies.

In a further variation, especially in case that a metallic powder material is used as the building material, the recording of the oscillations may also be performed in an inductive manner.

According to a further variation, the test specimen is co-built freely in the building room, separately from the base platform and separately from the object to be produced, and subsequently, it is removed and clamped and excited in order to oscillate.

According to a still further variation, the test specimen is provided on or at the object to be produced and is co-built when building the object. After measuring the frequencies, the test specimen is removed from the object.

According to a still further variation, several test specimen are co-built at different locations in the building space. In this connection, it is possible to find out inhomogeneities resulting from influences in the building space.

According to a still further embodiment, determination of the natural frequencies can be used in order to draw conclusions as to the building material. This can be useful, for example, in case of alloys in connection with powdery building material.

According to a still further embodiment, instead of flat bars or beams, other test specimens are built which show a low natural oscillation spectrum. Such test specimens may be, for example, tuning forks, bells or the like.

According to a second embodiment of the method, the test specimen is not co-built when manufacturing the desired object, but is used for quality determination and calibration of the laser sintering device and is built separately from the object itself in a separate building process. For this purpose, one or several test specimen are built before the start of a series job, and their natural frequency spectra are analyzed and compared to the one of a reference specimen. Subsequently, the parameters of the laser sintering device are adapted accordingly, so that the objects to be produced have the desired properties. A check can be carried out by means of co-building of test specimen in the series production.

The method is not restricted to a laser sintering process. It is applicable to all layer building methods, for example to stereolithography which uses, instead of a powdery material, a liquid, light-setting resin, to three-dimensional printing according to which the powdery building material is hardened selectively at the locations corresponding to the object via a binder, which is applied for example as a droplet particle onto the powder layer, or to selective mask sintering according to which, instead of a laser beam, a mask and an extensive light source are used. As a further layer building method to which the method according to the present invention is applicable, the so-called FDM-method (fused deposition modelling) or similar methods can be taken into account.

The invention claimed is:

1. Method of manufacturing a three-dimensional object according to which the object is built layer-wise from a building material to be solidified, comprising:
   building a test specimen on a removable building platform or at or on the object to be produced,
   exciting the test specimen to mechanical oscillations on the building platform or on the object after the building,
   determining natural frequencies of the oscillations of the test specimen, and
   determining material properties of the object to be produced from the determined natural frequencies of test specimen.

2. Method according to claim 1, wherein natural frequencies are determined acoustically and/or optically and/or in an inductive manner.

3. Method according to claim 1, wherein the test specimen has a geometric shape which comprises one or few dominant natural oscillation modes.

4. Method according to claim 1, wherein the test specimen is a bar.

5. Method according to claim 1, wherein the test specimen is built in a building process separate from the building process of the object to be produced.

6. Method according to claim 1, wherein the test specimen is built in the same building process as the object to be produced.

7. Method according to claim 1, wherein at least one determined natural frequency of the test specimen is compared to a known natural frequency of a reference specimen.

8. Method according to claim 1, wherein properties of the test specimen, of the building process and/or of the building device are determined from the determined natural frequencies.

9. Method according to claim 1, wherein the building material is applied in an application plane and in an application direction that is one of a first direction and a second direction opposite the first direction, and wherein the test specimen is built so that its main oscillation direction is essentially orthogonal to the application direction in the application plane.

10. Method according to claim 1, further comprising:
    producing an audio data file in an acoustic frequency analysis; and
    effecting a Fourier transformation in order to determine natural frequencies.

11. Method according to claim 1, further comprising recording the oscillations of the specimen in a contactless manner in an optical frequency analysis.

12. Method according to claim 1, wherein at least two test specimens are built at different locations in the building space, either simultaneously or at timely intervals.

13. Method according to claim 1, wherein the object is manufactured by layer-wise solidification of the building material by means of electromagnetic radiation or particle radiation at locations corresponding to the object in each layer.

14. Method according to claim 1, wherein powdery building material is used and wherein laser radiation is used as the electromagnetic radiation.

15. Method according to claim 1, wherein the three-dimensional object is an operative serial member and wherein the quality testing of the member is effected via determination of natural frequencies of a test specimen co-built with each of the members.

16. Method according to claim 1, wherein the determination of the natural frequencies is effected after a singular excitation.

17. Method according to claim 4, wherein the bar has a rectangular cross section.

18. Method according to claim 11, wherein the oscillations of the specimen are recorded with a rapid distance meter.

* * * * *